(12) United States Patent
Inoue

(10) Patent No.: US 10,206,822 B2
(45) Date of Patent: Feb. 19, 2019

(54) METHOD AND DEVICE FOR MANUFACTURING DISPOSABLE WORN ARTICLE

(71) Applicant: ZUIKO CORPORATION, Osaka (JP)

(72) Inventor: Daisuke Inoue, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 0 days.

(21) Appl. No.: 15/759,489

(22) PCT Filed: Sep. 12, 2016

(86) PCT No.: PCT/JP2016/076846
§ 371 (c)(1),
(2) Date: Mar. 12, 2018

(87) PCT Pub. No.: WO2017/056952
PCT Pub. Date: Apr. 6, 2017

(65) Prior Publication Data
US 2018/0256409 A1    Sep. 13, 2018

(30) Foreign Application Priority Data

Sep. 29, 2015    (JP) .................................. 2015-191499

(51) Int. Cl.
*B65G 29/00* (2006.01)
*B65G 47/84* (2006.01)
(Continued)

(52) U.S. Cl.
CPC ........ *A61F 13/15764* (2013.01); *A61F 13/15* (2013.01); *B65G 29/00* (2013.01);
(Continued)

(58) Field of Classification Search
None
See application file for complete search history.

(56) References Cited

U.S. PATENT DOCUMENTS 3,333,574 A * 8/1967 Harris .................. A01K 5/0208
119/56.1
5,025,910 A * 6/1991 Lasure .............. A61F 13/15764
198/377.04
(Continued)

FOREIGN PATENT DOCUMENTS

EP        3088164 A1    11/2016
JP    2010-530269 A     9/2010
(Continued)

OTHER PUBLICATIONS

International Search Report Issued in PCT/JP2016/076846 dated Nov. 22, 2016.

*Primary Examiner* — Kavel Singh
(74) *Attorney, Agent, or Firm* — Renner Otto Boisselle & Sklar, LLP

(57) ABSTRACT

The present device includes a rotor that is rotated around a cam drum and includes a plurality of units, each unit including: a mover that is guided by the cam drum and reciprocates in an axial direction of the cam drum by virtue of the rotation of the rotor; a first belt linked to the mover; a first pulley and a second pulley that rotate with the first belt wound therebetween; a pad that reciprocates in the axial direction in accordance with the reciprocation of the mover, while holding a sheet piece; a second belt linked to the pad; a third pulley and a fourth pulley that rotate with the second belt wound therebetween; and a transmission mechanism that transmits the rotation of the second pulley to the third pulley and changes a rotation speed of the third pulley with respect to a rotation speed of the second pulley.

11 Claims, 10 Drawing Sheets

(51) Int. Cl.
- *B65G 47/74* (2006.01)
- *A61F 13/15* (2006.01)
- *F16H 7/08* (2006.01)
- *F16H 9/04* (2006.01)
- *F16H 25/12* (2006.01)

(52) U.S. Cl.
CPC ............... *F16H 7/08* (2013.01); *F16H 9/04* (2013.01); *F16H 25/12* (2013.01); *B65G 2201/0229* (2013.01)

(56) References Cited

U.S. PATENT DOCUMENTS

| | | | |
|---|---|---|---|
| 6,880,694 B2* | 4/2005 | Sowden | A23G 3/04 198/471.1 |
| 7,240,785 B2* | 7/2007 | Sowden | A23G 3/04 198/471.1 |
| 7,431,145 B2* | 10/2008 | Ganter | B42C 19/08 198/626.1 |
| 2010/0192739 A1 | 8/2010 | Piantoni et al. | |
| 2015/0024919 A1 | 1/2015 | Shimada | |
| 2015/0297416 A1 | 10/2015 | Piantoni et al. | |

FOREIGN PATENT DOCUMENTS

| | | |
|---|---|---|
| WO | WO 2013-157533 A1 | 10/2013 |
| WO | WO 2014-087293 A1 | 6/2014 |
| WO | WO 2015-098533 A1 | 7/2015 |

* cited by examiner

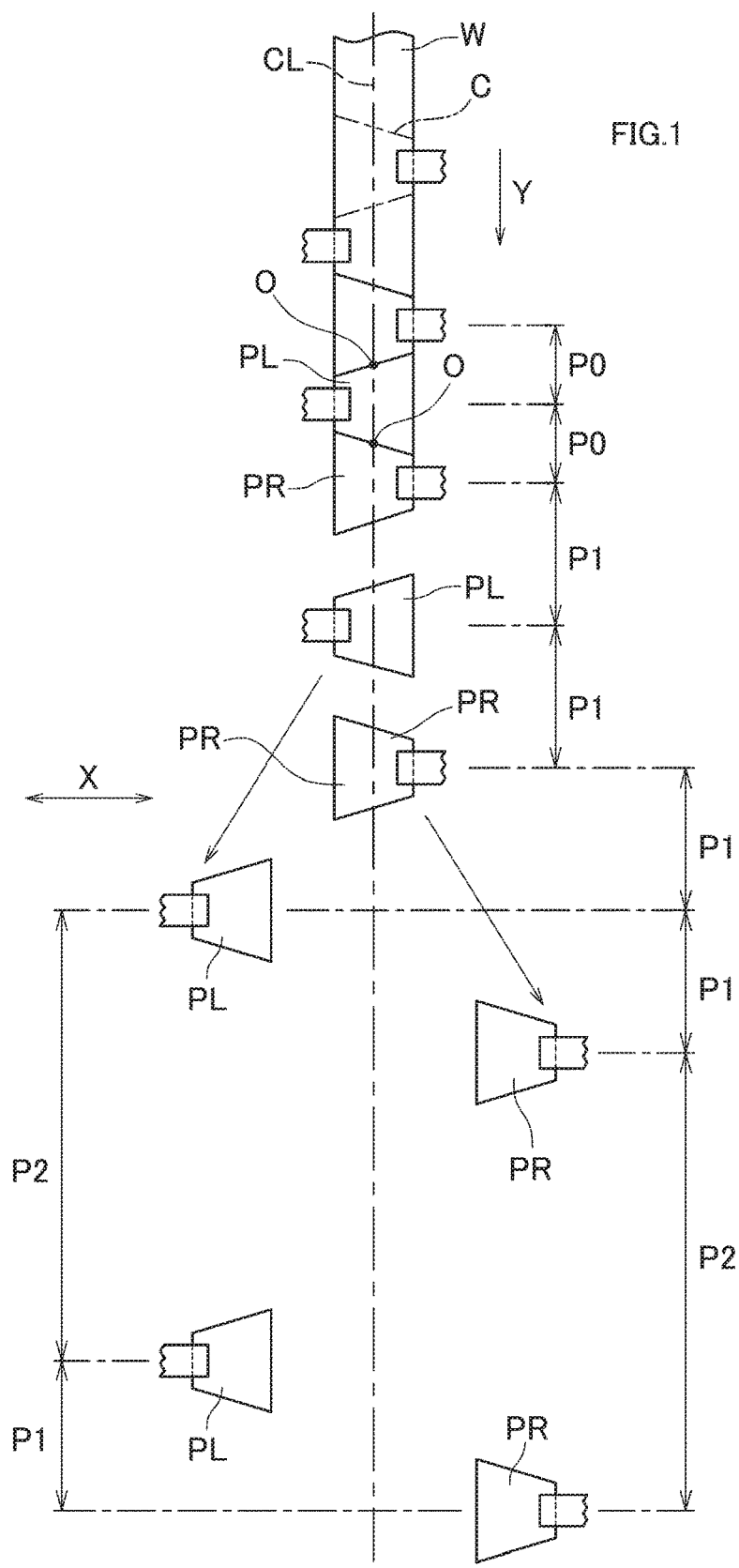

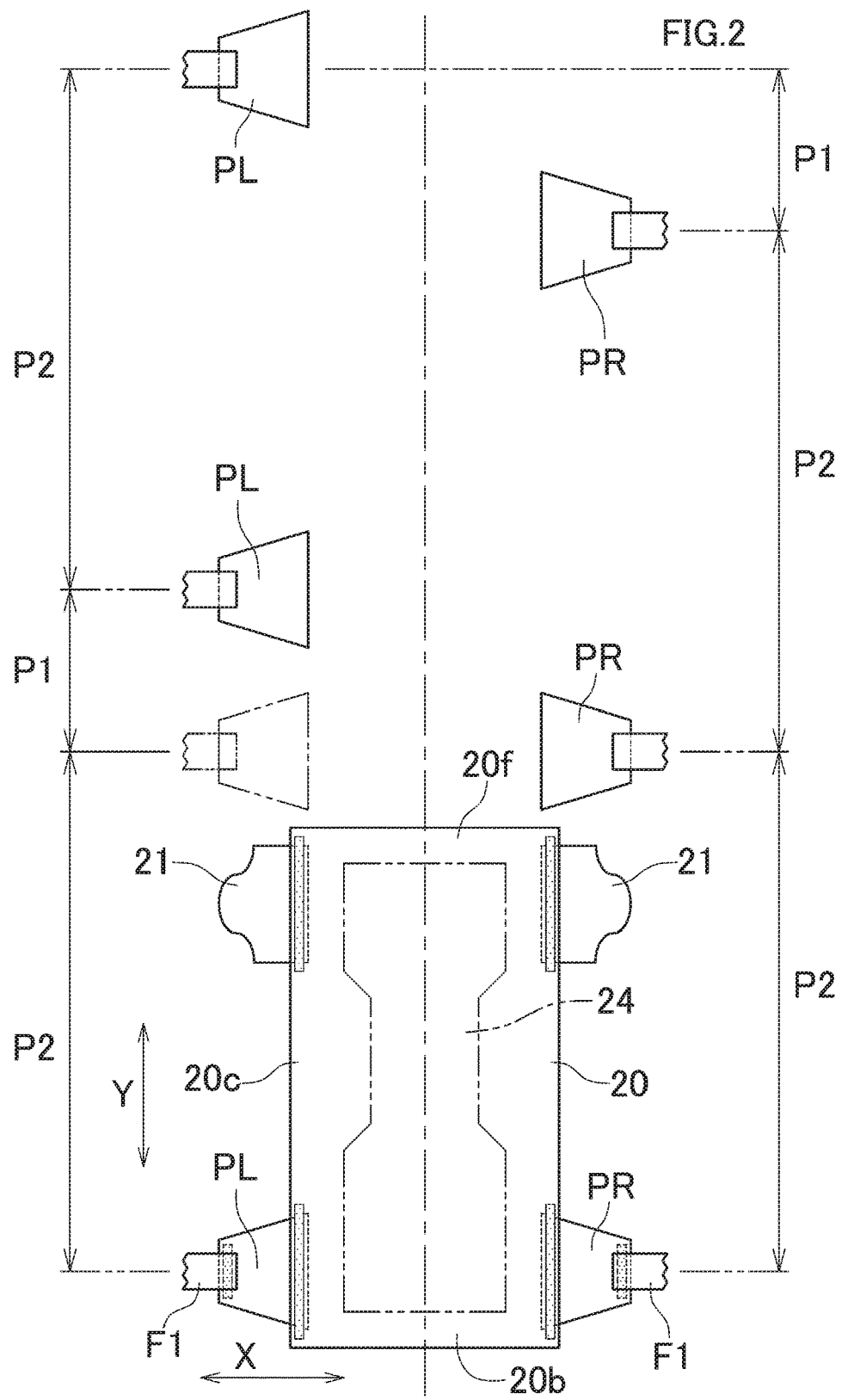

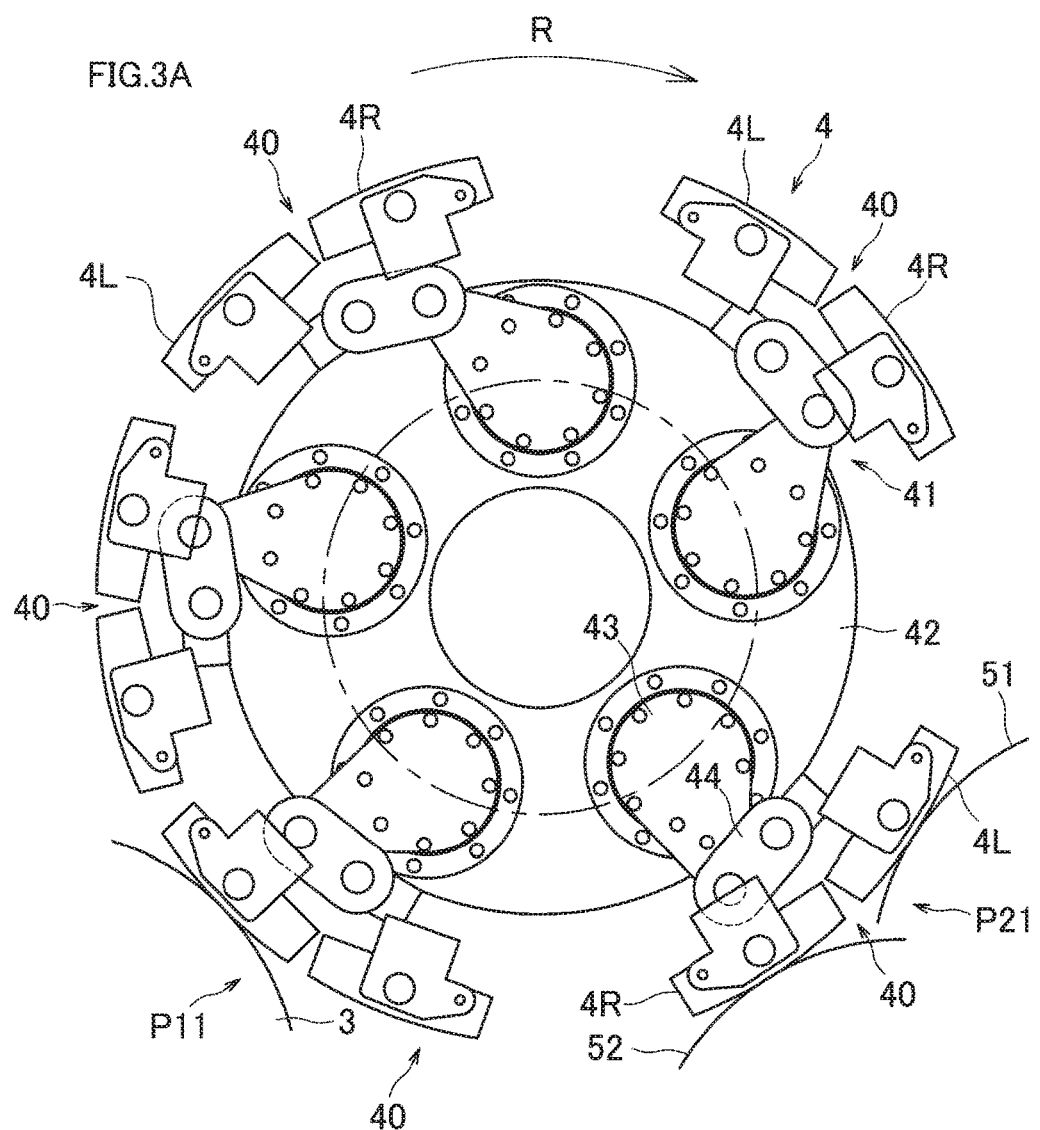
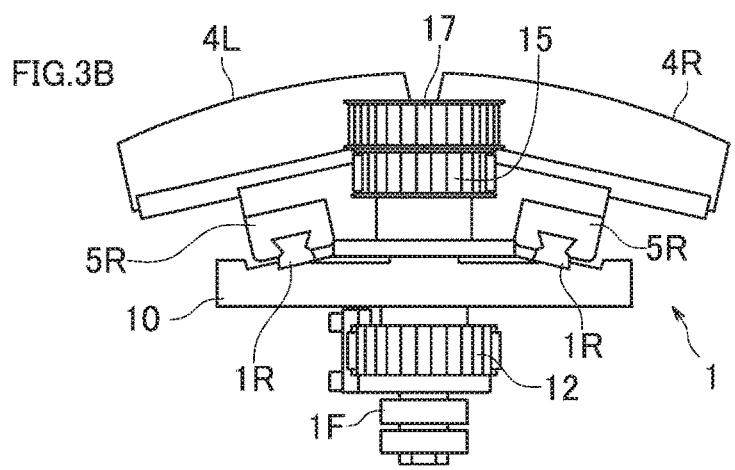

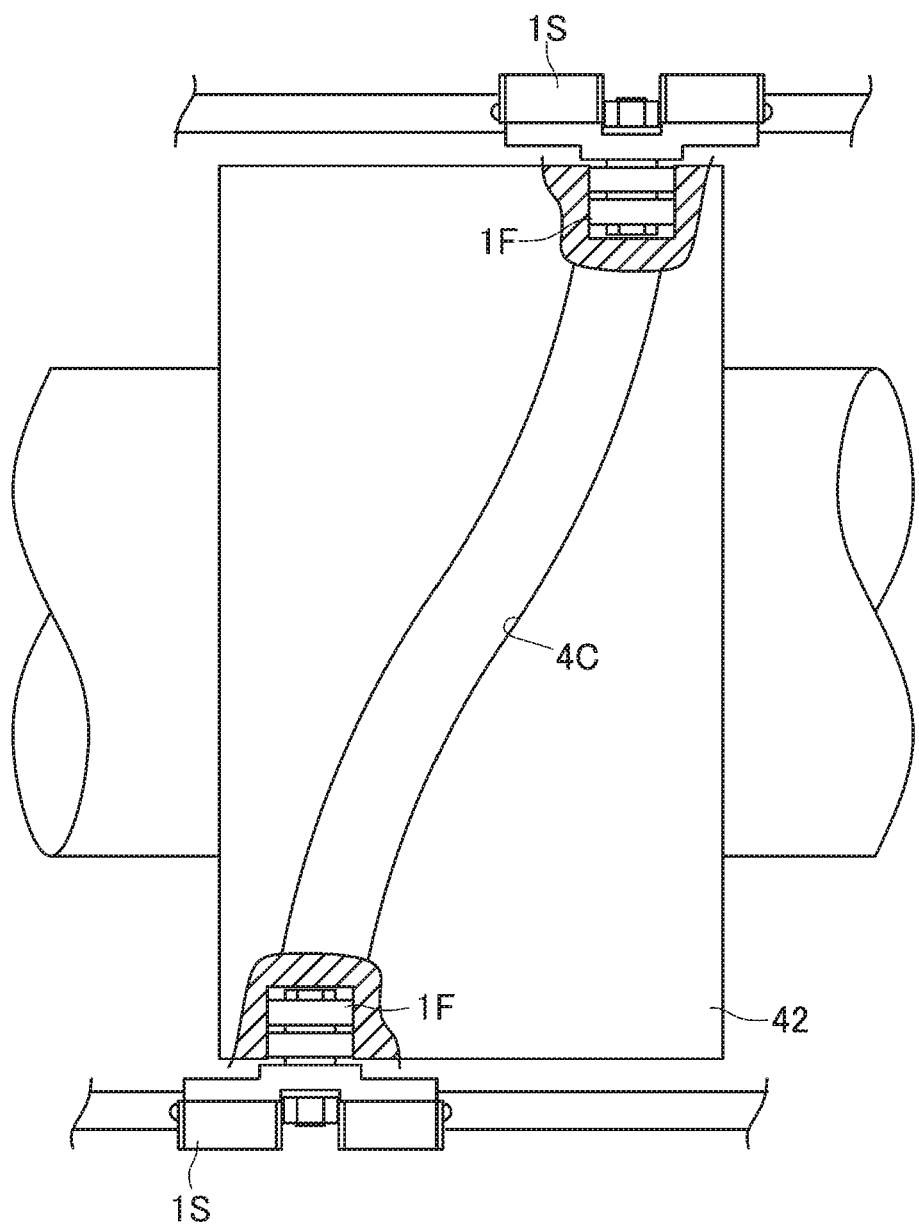

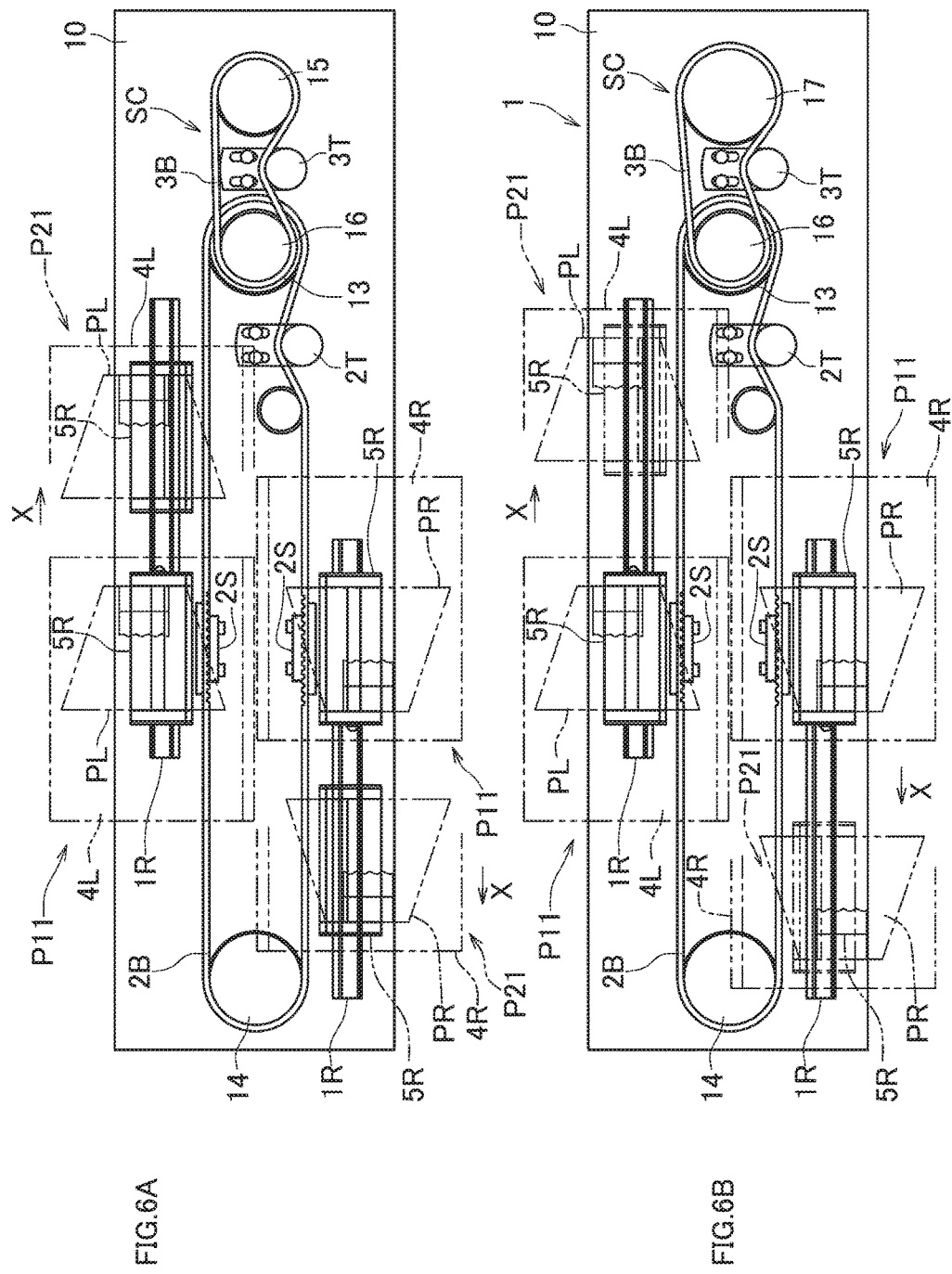

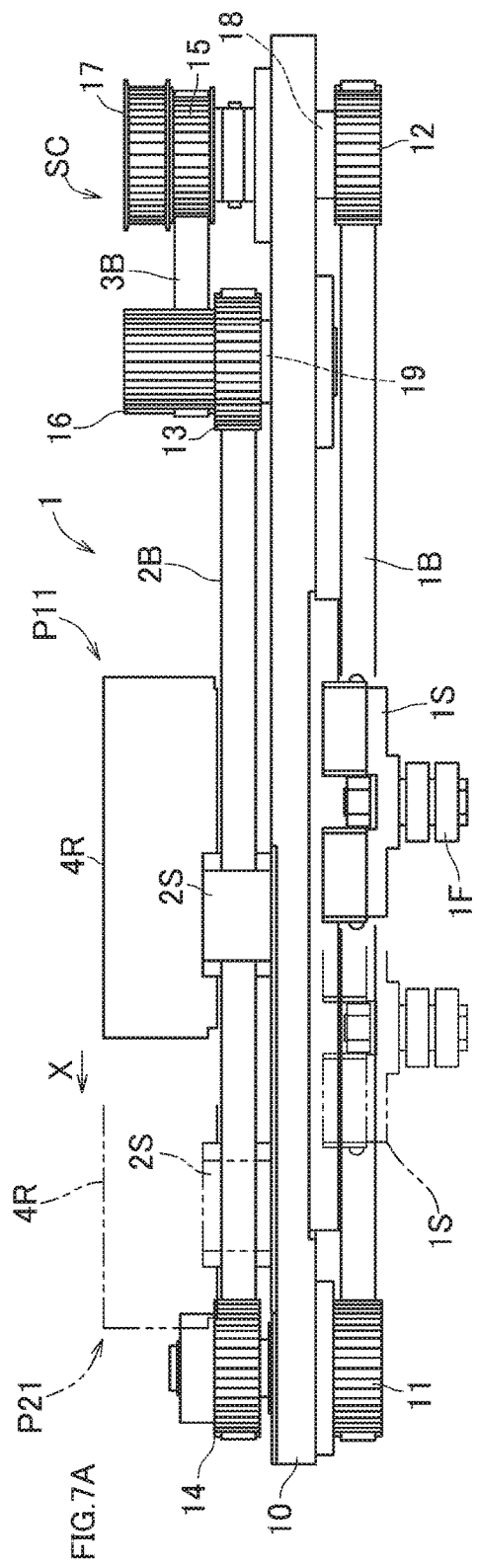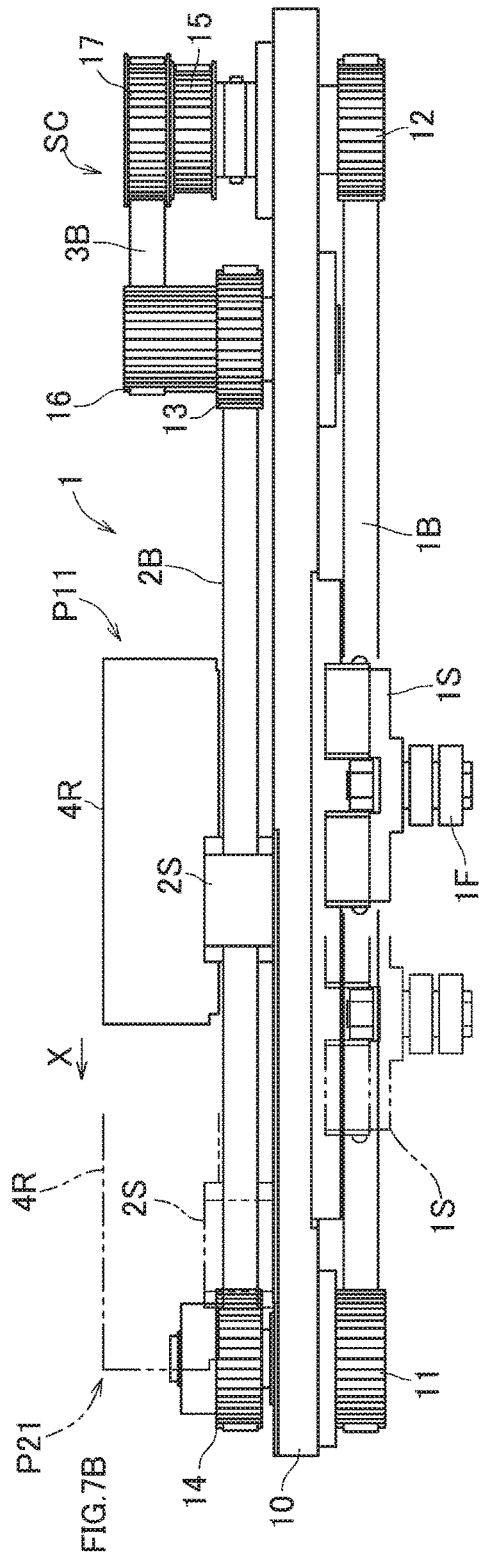

METHOD AND DEVICE FOR MANUFACTURING DISPOSABLE WORN ARTICLE

TECHNICAL FIELD

The present invention relates to a method and a device for manufacturing a disposable worn article.

BACKGROUND ART

As a device for manufacturing a worn article of this type, devices for attaching a set of panels on the left side and the right side in the girth direction of the body portion of the diaper (the first and second patent documents) are known in the art. Also, a rotor including a plurality of units that rotate around a cam drum is known in the art (the third patent document).

CITATION LIST

Patent Literature

[First Patent Document] JP2010-530269A (FIGS. 1 to 6)
[Second Patent Document] WO2013/157533A1 (FIG. 1)
[Third Patent Document] U.S. Pat. No. 9,265,670B2 (FIG. 1)
[Fourth Patent Document] WO2014/087293A1 (FIGS. 3, 9)

FIG. 10 shows a portion of a device disclosed in WO2014/087293A1. In this figure, a plurality of units 100 each include a pad 101 for holding a side panel, and a rail 103 for guiding the pad 101 so that the pad 101 moves in the axial direction of a cam drum 102. Each unit 100 is guided by the cam drum 102 and the guide rail 103 to reciprocate in the axial direction, while rotating around the cam drum 102. Thus, panels held on the pads 101 are placed on the diaper body portion with a constant interval therebetween.

SUMMARY OF INVENTION

However, there are diapers of different sizes. Diapers of different sizes have different distances between a pair of, left and right, panels. When manufacturing diapers of different sizes, it is necessary, with the conventional technique described above, to replace the cam drum. Thus, changing the size is troublesome and costly.

Even where only one type of a standard size is manufactured, a similar problem will occur when there is a change to the standard size itself.

It is an object of the present invention to provide a device and a method for manufacturing different types of disposable worn article having different sizes, without replacing the cam drum.

The device of the present invention includes:
a cam drum; and
a rotor that is rotated around the cam drum, wherein:
the rotor includes a plurality of units; and
each of the units includes:
a mover that is guided by the cam drum and reciprocates in an axial direction parallel to an axial line of the cam drum by virtue of the rotation of the rotor (i.e., while the rotor rotates);
a first belt linked to the mover;
a first pulley and a second pulley between which the first belt is wound and which rotate together with the first belt;
a pad that reciprocates in the axial direction in accordance with the reciprocation of the mover, while holding a sheet piece, which is a part of the worn article;
a second belt linked to the pad;
a third pulley and a fourth pulley between which the second belt is wound and which rotate together with the second belt; and
a transmission (speed-changing) mechanism that transmits the rotation of the second pulley to the third pulley and changes a speed of reciprocation of the pad with respect to a speed of reciprocation of the mover.

Where worn articles of a first size and a second size are manufactured using the device of the present invention,
the transmission mechanism is set to a first speed ratio when manufacturing a worn article of the first size; and
the transmission mechanism is set to a second speed ratio different from the first speed ratio when manufacturing a worn article of the second size.

That is, the speed ratio (transmission ratio) of the transmission mechanism is changed when changing the size of the worn article to be manufactured.

For example, the speed ratio may be changed by changing the third pulley to another third pulley having a different diameter.

According to the present invention, it is possible to manufacture different disposable worn articles of different sizes without replacing the cam drum. Therefore, changing the size is neither troublesome nor costly.

BRIEF DESCRIPTION OF DRAWINGS

FIG. 1 is a conceptual diagram showing a method for manufacturing a worn article of the present invention, showing a part of a step of manufacturing a diaper of a first size.
FIG. 2 is a conceptual diagram showing the rest of the same step.
FIG. 3A is a schematic side view showing a manufacturing device of the present invention,
and FIG. 3B is a front view of a unit.
FIG. 4 is a schematic side view showing a cam drum.
FIG. 6A and FIG. 6B are plan views showing a unit when manufacturing an article of a first size and an article of a second size, respectively.
FIG. 7A and FIG. 7B are side views of the unit when manufacturing an article of the first size and an article of the second size, respectively.

DESCRIPTION OF EMBODIMENTS

Figure 5:
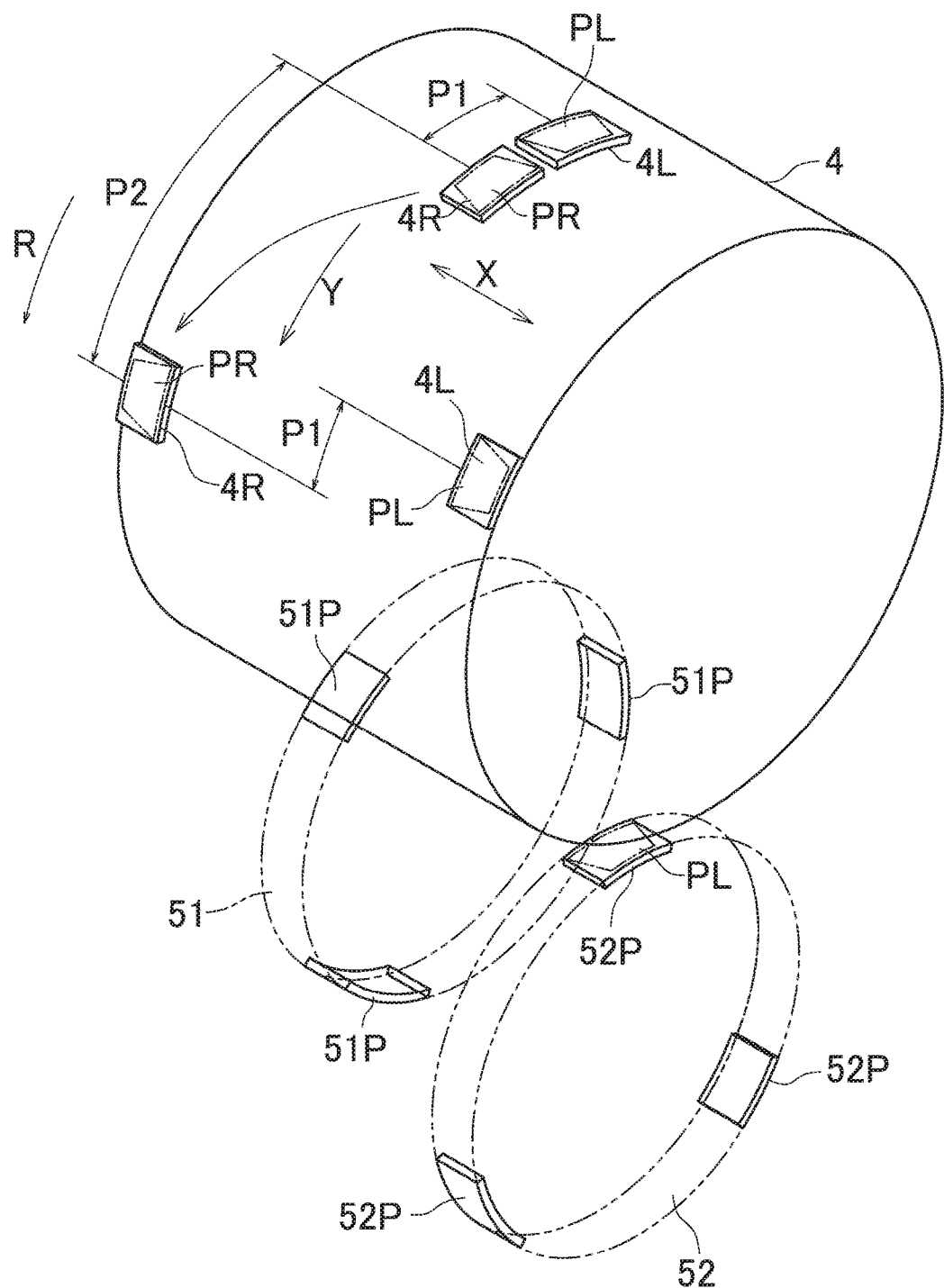
FIG. 5 is a conceptual perspective view showing an interval-increasing drum, a first roller and a second roller.

Preferably, the transmission mechanism is present (exists) between the second pulley and the third pulley, and changes a rotation speed of the third pulley with respect to a rotation speed of the second pulley, thereby changing the speed of reciprocation of the pad with respect to the speed of reciprocation of the mover.

In this case, articles of different sizes can be manufactured only by changing the speed ratio of the transmission mechanism that is present between the second pulley and the third pulley, without changing (replacing) the second pulley and the third pulley themselves.

Preferably, the transmission mechanism includes:

a fifth pulley to which a torque of the second pulley is input;

an endless third belt that is wound around the fifth pulley and is driven by the rotation of the fifth pulley; and a sixth pulley around which the third belt is wound, which is rotated by the rotation of the third belt, and which inputs a torque thereof (i.e., of the sixth pulley) to the third pulley.

In this case, when changing the size of the worn article to be manufactured, the method further includes at least one of the step of changing the fifth pulley to another fifth pulley having a different diameter and the step of changing the sixth pulley to another sixth pulley having a different diameter.

In this case, articles of different sizes can be manufactured by a simple operation of changing the fifth or sixth pulley to a pulley having a different diameter.

Preferably, the transmission mechanism further includes a seventh pulley that is placed on the same (an identical) axis with the fifth pulley and has a diameter different from the fifth pulley, or further includes a seventh pulley that is placed on the same (an identical) axis with the sixth pulley and has a diameter different from the sixth pulley.

In this case, articles of different sizes can be manufactured by a very simple operation of re-winding the third belt, which has been wound around the fifth or sixth pulley, around the seventh pulley.

Preferably, the device further includes a tensioner for adjusting a tension of the third belt.

In this case, even when the third belt is re-wound around a pulley having a different diameter, the tension of the third belt can be set to an intended tension.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

An embodiment of the present invention will now be described with reference to the drawings.

First, before describing a manufacturing method and a manufacturing device of the present invention, an example of a worn article that can be manufactured by the present manufacturing method will be described.

As shown in FIG. 2, the present diaper includes an absorbent body portion 20, and a pair of side panels (an example of sheet pieces) PL, PR and a pair of tab members 21, 21 attached to the body portion 20.

The body portion 20, when worn, covers the front girth area, the crotch area and the rear girth area of the wearer. The body portion 20 includes a front torso portion 20f, a crotch portion 20c and a rear torso portion 20b corresponding respectively to these areas.

When worn, the panels PL, PR are each located between the front and rear torso portions 20f, 20b in the girth direction X. The panels PL, PR are attached to the left side and the right side, respectively, of an end portion of the body portion 20 in the longitudinal direction Y. For example, the panels PL, PR are attached to the rear torso portion 20b while protruding from the left side and the right side of the rear torso portion 20b of the body portion 20. Note that the panels PL, PR may be attached to the front torso portion 20f.

On the other hand, the tab members 21 are attached to the left side and the right side of the front torso portion 20f of the body portion 20. Note that the tab members 21 may be omitted.

The panels PL, PR may be formed by providing elastic threads (an example of an elastic member) sandwiched between two sheets of a non-woven fabric, for example. The panels PL, PR may be in a shrunk state with gathers formed thereon, as the elastic threads shrink in the girth direction X, under no load.

Note that the method disclosed in JPS63-243309A may be used as the method for placing elastic threads on the panels PL, PR.

Instead of using elastic threads, the panels PL, PR may be formed from a stretchable non-woven fabric having stretchability.

A first touch fastener (an example of an attachment element) F1 may be attached to the inner surface side (the side to be in contact with the skin when worn) of the panels PL, PR. On the other hand, a second touch fastener (not shown) capable of being touch-fastened to the first touch fastener F1 may be attached to the outer surface side (the side to be exposed to the outside when worn) on the front torso portion 20f side of the body portion 20. When wearing the present diaper, one puts the side panels PL, PR around the torso of the wearer while holding the tab members 21, and attaches the first touch fasteners F1 of the side panels PL, PR to the second touch fastener, thus putting the present diaper on the wearer.

Note that if the outer surface side of the body portion 20 is formed from a material to which the first touch fastener F1 can be attached, the second touch fastener may be omitted. The body portion 20 and the panels (PR, PL) may be provided with an adhesive tape and an area where the adhesive tape is attached, respectively, instead of the touch fasteners.

The body portion 20 may include, for example, a pair of cuffs (anti-leak walls) to be in contact with the surface of the wearer, a liquid-permeable top sheet, a liquid-absorbing absorbent core 24, a liquid-impermeable back sheet, etc.

Note that the body portion 20 may include, for example, leg elastic threads. Moreover, the cuffs may be omitted, and elastic threads may be provided for shrinking the cuffs in the Y direction. The back sheet may be an air-permeable, waterproof sheet. The back sheet may be a stretchable sheet.

Next, a part of an example of a manufacturing apparatus will be described.

As shown in FIG. 3A, the present manufacturing apparatus includes a first re-pitch drum 3, an interval-increasing drum (manufacturing device) 4, a first roller 51, a second roller 52 and a conveyer device (not shown).

The re-pitch drum 3 receives panels (PL, PR) shown in FIG. 1 from a supply device (not shown). The supply device (not shown) severs a continuous web W successively along cut-off lines C with alternating inclinations, as shown in FIG. 1, thereby successively producing panels PL, PR.

The virtual cut-off lines C may be non-parallel to the width direction X, and the tip portion of the continuous web W may be severed by a cutter (not shown) successively along the non-parallel cut-off lines C, thereby producing the panels PL, PR. For example, the panels PL, PR may be trapezoidal, and the panels PL, PR may be shaped to be in point symmetry with each other about the point O on the center line CL. The shape of the panels PL, PR may be a parallelogram, a square or a rectangular.

The first re-pitch drum 3 of FIG. 3A includes a plurality of left pads and right pads whose interval increases in the rotation direction (circumferential direction), and the pads then come closer to each other in the rotation direction. After receiving the panels (PL, PR) by the first re-pitch drum well known in the art, the interval (the distance between the panels) P0 in the flow direction Y between the panels PL, PR of FIG. 1 is increased to the interval P1.

Note that the first re-pitch drum 3 may be the drum disclosed in US2006/0151093A1 or JPS63-317576A, whose disclosure is herein incorporated by reference in its entirety.

The interval-increasing drum 4 of FIG. 3A includes a rotor 40 that is rotated, and a plurality of sets of link mechanisms 41 and a plurality of sets of interval-increasing units 1 (FIG. 6A) forming a part of the rotor 40.

With the present interval-increasing drum 4, a first link 43 and a second link 44 of the link mechanism 41 rotate along cam grooves formed on the side surface of a cam drum 42, so that a plurality of sets of interval-increasing units 1, 1 (FIG. 6A) revolve at a periodically varying speed.

That is, the present interval-increasing drum 4 of FIG. 3A may be a second re-pitch drum. A plurality of sets of interval-increasing units 1 (FIG. 6A) revolve while the sets repeatedly come close to and move away from each other in the circumferential direction of the interval-increasing drum 4. Note that in this example, the interval-increasing drum 4 successively receives panels from the first re-pitch drum 3, and hands over the panels alternately to the first and second rollers 51, 52.

The interval-increasing drum 4 of FIG. 3A is placed downstream of the first re-pitch drum 3 to increase the interval (the distance) in the width direction X between a set of panels (PL, PR) adjacent to each other, of the plurality of panels (PL, PR) of FIG. 1. The interval-increasing drum 4 may form a second re-pitch drum that increases the set-to-set interval P2 between (i) a set of panels PL, PR, which are separated from each other in the flow direction Y and (ii) another set of panels PL, PR adjacent to the separated set of panels.

The interval-increasing drum 4 conceptually shown in FIG. 5 includes a plurality of left pads 4L and a plurality of right pads 4R. While the interval-increasing drum 4 makes one rotation, the interval in the width direction X between the pads 4L, 4R and the flow direction Y increase and then the pads 4L, 4R return to the original state.

That is, as the interval-increasing drum 4 rotates in the circumferential direction R, a step is performed, wherein the right pad 4R moves toward one side of the interval-increasing drum 4 and the left pad 4L moves toward the other side of the interval-increasing drum 4, thereby increasing the interval in the width direction X between the pad 4R and the pad 4L, while the interval-increasing drum 4 forming the second re-pitch drum increases the interval in the flow direction Y between pads 4R, 4R (4L, 4L) that are adjacent to each other in the flow direction Y. In this step, as shown in FIG. 1, the interval between panels PL, PL (PR, PR) that are adjacent to each other in the flow direction is increased from (2*P1) to P2.

In the placement step to be described below, after the pads 4R, 4L of FIG. 5 hand over the panels PL, PR to the first and second rollers 51, 52, respectively, the width interval between the right and left pads 4R, 4L returns to the original state for the pads 4R, 4L to again receive the panels PL, PR, and the interval in the flow direction between the re-pitched pads also returns to the original interval.

The structure of a drum disclosed in JP2006-230438A, for example, may be employed as the structure of the interval-increasing drum 4 described above, and the disclosure thereof is herein incorporated by reference in its entirety.

In FIG. 3A, the first and second rollers 51, 52 are placed downstream of the interval-increasing drum 4. The rollers 51, 52 place the set of panels PR, PL, respectively, of FIG. 2 on the body portion 20.

As shown in FIG. 5, the first and second rollers 51, 52 include first and second pads 51P, 52P for holding the panels PL, PR. The first pads 51P and the second pads 52P are placed away from each other in the width direction X.

Note that the details of the structure of the first and second rollers 51, 52 described above are disclosed in WO2013/157533A1, supra, and the disclosure thereof is herein incorporated by reference in its entirety.

Next, the interval-increasing mechanism of the present interval-increasing drum 4 will be described.

As shown in FIG. 4, a cam groove 4C may be formed on the outer surface of the cam drum 42. The cam groove 4C is provided in a loop extending in the circumferential direction of the cam drum 42.

A cam follower 1F of each interval-increasing unit 1 (FIG. 3A) fits in the cam groove 4C. Each cam follower 1F is attached to a mover 1S. The mover 1S is guided along the cam groove 4C so as to reciprocate in the axial direction parallel to the axial line of the interval-increasing drum 4 by virtue of the rotation of the interval-increasing unit in the circumferential direction.

The interval-increasing unit 1 shown in FIG. 7A rotatably supports first to seventh pulleys 11 to 17 on a frame 10. As shown in FIG. 3B, the frame 10 is provided for each interval-increasing unit 1 and rotates in the circumferential direction R of FIG. 3A.

On one side of the frame 10 of FIG. 7A, an endless first belt 1B is wound between the first pulley 11 and the second pulley 12. The first mover 1S is attached to the first belt 1B.

On the other side of the frame 10 of FIG. 7A, an endless second belt 2B is wound between the third pulley 13 and the fourth pulley 14. A pair of second movers 2S, 2S of FIG. 6A is attached to the second belt 2B.

In FIG. 7A, the torque of the second pulley 12 is input to the fifth pulley 15 via a rotation shaft 18. An endless third belt 3B is wound between the fifth pulley 15 and the sixth pulley 16. The fifth pulley 15 and the seventh pulley 17 may be fixed on the same axis, and the third belt 3B is wound selectively around either the fifth pulley 15 or the seventh pulley 17, as shown in FIG. 7A and FIG. 7B. The sixth pulley 16 inputs its torque to the third pulley 13 via a rotation shaft 19.

That is, in the present embodiment, the fifth to seventh pulleys 15 to 17 and the third belt 3B together form a transmission mechanism SC. The transmission mechanism SC of this example is present between the second pulley 12 and the third pulley 13, and the transmission mechanism SC transmits the torque of the second pulley 12 to the third pulley 13 and changes the rotation speed of the third pulley 13 with respect to the rotation speed of the second pulley 12.

Note that each of the pulleys may be a toothed pulley. Each of the belts may be a timing belt.

As shown in FIG. 6A, a pair of second movers 2S, 2S are attached to sides of the second belt 2B that are facing each other. The second movers 2S, 2S are attached respectively to the pads 4L, 4R, and are caused to reciprocate in opposite directions by the rotation of the pulleys and the belts, thereby reciprocating the pads 4L, 4R in opposite directions.

Two pads 4L, 4R are attached to the frame 10 of FIG. 3B via two rails 1R and sliders 5R. Therefore, the pads 4L, 4R attached to the second movers 2S of FIG. 6A move in the axial direction X, while respectively holding the panels PL, PR thereon, in accordance with the reciprocation of the first mover 1S (FIG. 7A).

Each of the first and fourth pulleys 11, 14 of FIG. 7A is individually rotatably supported on the frame 10. The second, fifth and seventh pulleys 12, 15, 17 are attached to one rotation shaft 18, and rotate in sync with each other at the same rotation speed (number of revolutions/min). The third and sixth pulleys are attached to one rotation shaft 19, and rotate in sync with each other at the same rotation speed.

The second pulley 12 is caused to rotate by the rotation of the first belt 1B, which is caused by the reciprocation of the first mover 1S, and the rotation is transmitted to the fifth pulley 15. The rotation of the fifth pulley 15 is transmitted to the sixth pulley 16 via the third belt 3B, thereby rotating the third pulley 13 together with the shaft 19.

As the second belt 2B is rotated by the rotation of the third pulley 13 of FIG. 6A, a pair of pads 4L, 4R reciprocate in opposite directions together with the second movers 2S.

Thus, a pair of pads 4L, 4R of FIG. 5 move in the axial direction X so as to move away from each other, while rotating in the circumferential direction R while holding the panels PL, PR, respectively. Note that the pads 4L, 4R come close to each other while rotating after handing over the panels to the rollers 51, 52 of FIG. 3A.

That is, the panels PL, PR held on a set of pads 4L, 4R come close to each other at a receiving position P11 of FIG. 3A and FIG. 6A, and significantly move away from each other in the axial direction X at a hand-over position P21 of FIG. 3A and FIG. 6A. Note that by rotating from the hand-over position P21 to the receiving position P11 of FIG. 3A, the pads 4L, 4R, which were away from each other in the axial direction X at the hand-over position P21 of FIG. 6A, come close to each other as they are at the receiving position P11.

The second and third belts 2B, 3B of FIG. 6A are provided with tensioners 2T, 3T for adjusting the tensions of the belts 2B, 3B, respectively.

Next, an example of a method for manufacturing a diaper of a particular size will be described.

The manufacturing method of the present embodiment may include a severing step, a first re-pitch step, an interval-increasing step, a second re-pitch step, a receiving step and a placement step to be described below.

As shown in FIG. 1, in the severing step, the tip portion in the flow direction Y of the continuous web W, which is continuous in the flow direction Y, is severed by a cutter (not shown) successively along the virtual cut-off line C extending in the width direction X, thereby successively producing a plurality of panels PL, PR. The panels PL, PR produced by the severing are received by the first re-pitch drum 3 (FIG. 3A), and then the interval therebetween in the flow direction Y of FIG. 1 is increased from P0 to P1 of FIG. 1. Thus, the first re-pitch step is performed.

After the first re-pitch step, the panels PL, PR of FIG. 1 are handed over from the first re-pitch drum 3 to the interval-increasing drum 4 of FIG. 3A. On the interval-increasing drum 4, the interval in the width direction X between a set of panels PL, PR, adjacent to each other, of the plurality of panels PL, PR of FIG. 1 is increased. Thus, the interval-increasing step is performed.

At the same time with the interval-increasing step, the second re-pitch step of increasing the set-to-set interval between a set of panels PL, PR and another, adjacent set of panels PL, PR, which are separated from each other in the flow direction Y may be performed. That is, the interval between panels PR (PL) that are adjacent to each other in the flow direction Y may be increased to P2.

In this process, a phase shift (phase difference) of the pitch P1 of FIG. 1 is present between the set of panels PL, PR.

After the interval-increasing step and the second re-pitch step, the receiving step of receiving, on the first and second rollers 51, 52, the panels PL, PR from the interval-increasing drum 4 of FIG. 3A is performed. Moreover, a step of placing each of the set of panels PR, PL of FIG. 2 on the body portion 20 is performed. That is, after the receiving step, the placement step shown in FIG. 2 is performed. In this placement step, the panels PL, PR from the first and second rollers 51, 52 (FIG. 5) are placed on opposite sides of the body portion 20. Note that the details of the placement step are disclosed in WO2013/157533A1 (U.S. Pat. No. 9,265,670B2), supra, and the disclosure thereof is herein incorporated by reference in its entirety.

Next, a case where there is a change to the size of the worn article to be manufactured will be described.

Figure 8:
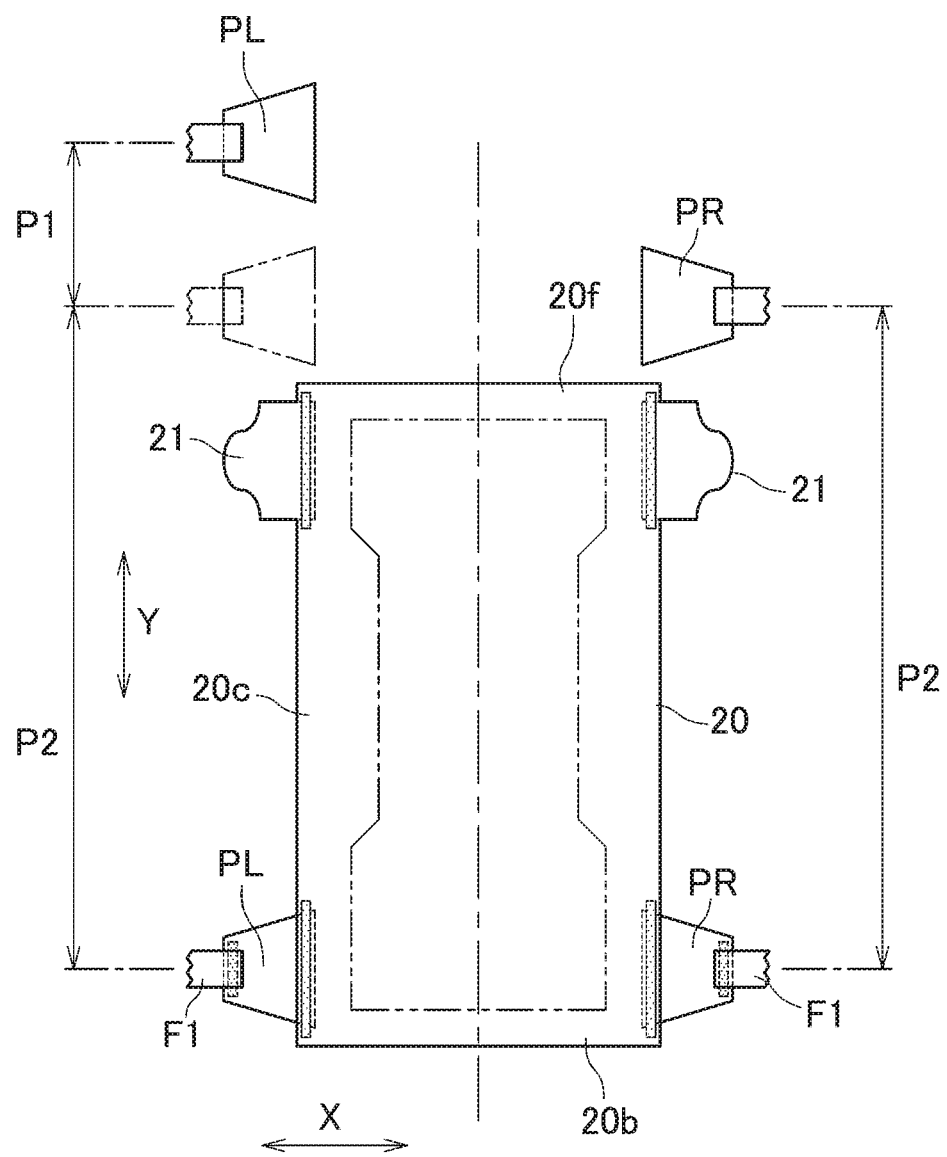
FIG. 8 is a conceptual diagram showing a diaper of the second size and a part of a method for manufacturing the same.

FIG. 2 shows a diaper of a first, small size, whereas FIG. 8 shows a diaper of a second, large size.

The set-to-set interval P2 of the diaper of the second size of FIG. 8 may be greater than or equal to the set-to-set interval P2 of the diaper of the first size of FIG. 2.

The distance in the width direction X between the panels PL, PR of the diaper of the second size of FIG. 8 is greater than the distance in the width direction X between the panels PL, PR of the diaper of the first size of FIG. 2.

In FIG. 7A, in the present embodiment, the diameter of the fifth pulley 15 is smaller than the diameter of the seventh pulley 17, for example. The second speed ratio of the sixth pulley with respect to the seventh pulley 17 is greater than the first speed ratio of the sixth pulley with respect to the fifth pulley 15.

Therefore, when manufacturing a diaper of the first, small size, a setting is used in which the third belt 3B is wound between the fifth pulley 15 and the sixth pulley 16 as shown in FIG. 7A. On the other hand, when manufacturing a diaper of the second, large size, a setting is used in which the third belt 3B is wound between the seventh pulley 17 and the sixth pulley 16 as shown in FIG. 7B.

When manufacturing a diaper of the first size, the transmission mechanism SC is set to the first speed ratio as shown in FIG. 6A. Then, the tension of the third belt 3B is adjusted by the tensioner 3T (FIG. 6A). Thereafter, the diaper of the first size is manufactured by a method similar to that described above.

When manufacturing a diaper of the second size, the transmission mechanism SC is set to the second speed ratio as shown in FIG. 6B. Then, the tension of the third belt 3B is adjusted by the tensioner 3T (FIG. 6A). Thereafter, the diaper of the second size is manufactured by a method similar to that described above.

In the present embodiment, the speed ratio is changed by first operating the tensioner 3T of FIG. 6A to slack the tension of the third belt, and moving the third belt 3B in the axial direction of the shafts 18, 19 so that the third belt 3B is wound between the sixth pulley 16 and the seventh pulley 17 as shown in FIG. 7B, without removing the transmission mechanism SC of FIG. 7A from the unit 1. Then, the tensioner 3T of FIG. 6B is operated to adjust the tension of the third belt 3B.

Figure 9A:
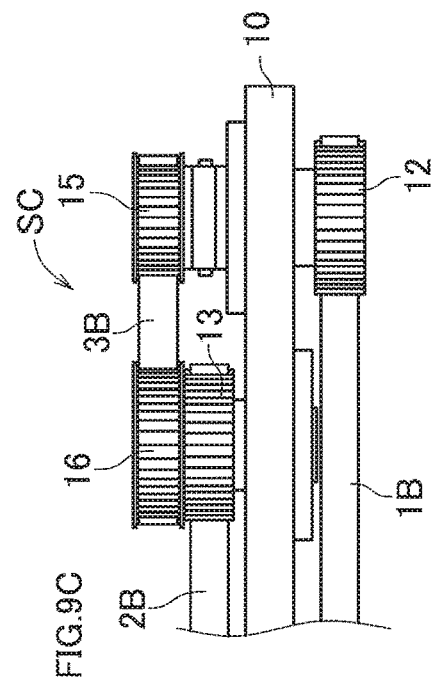
FIG. 9A and FIG. 9B are side views showing alternative examples of a transmission mechanism.
Figure 9B:
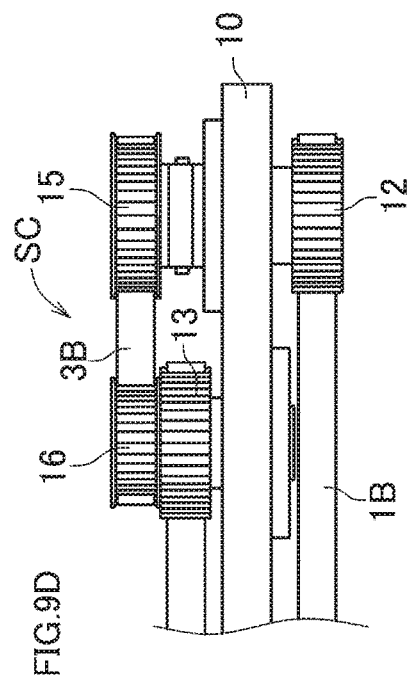

FIG. 9A and FIG. 9B show another example of the transmission mechanism SC.

In these figures, the fifth pulley 15 placed on the same axis with the second pulley 12 is elongated in the axial direction. The third belt 3B is wound between either the sixth pulley 16 or the seventh pulley 17 and the fifth pulley 15.

Figure 9C:
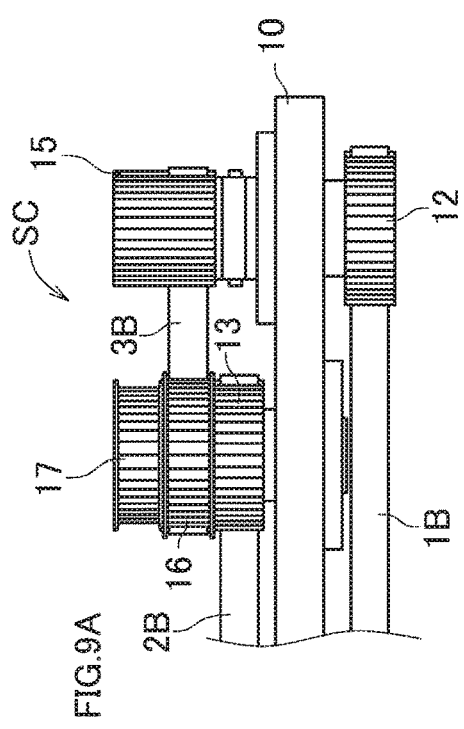
FIG. 9C and FIG. 9D are side views showing other alternative examples of the transmission mechanism.
Figure 9D:
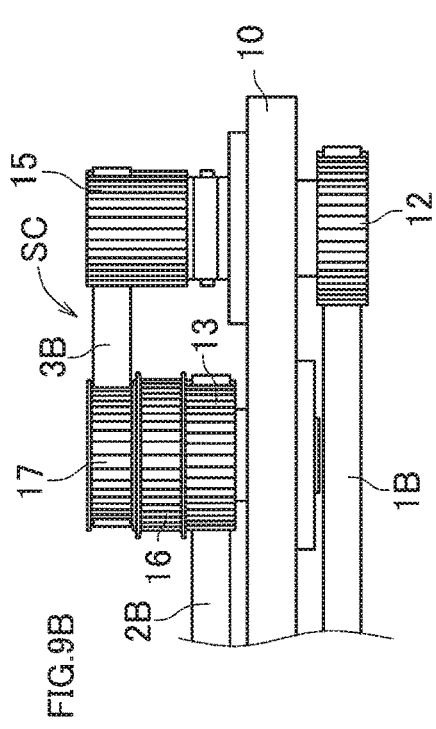
Figure 10:
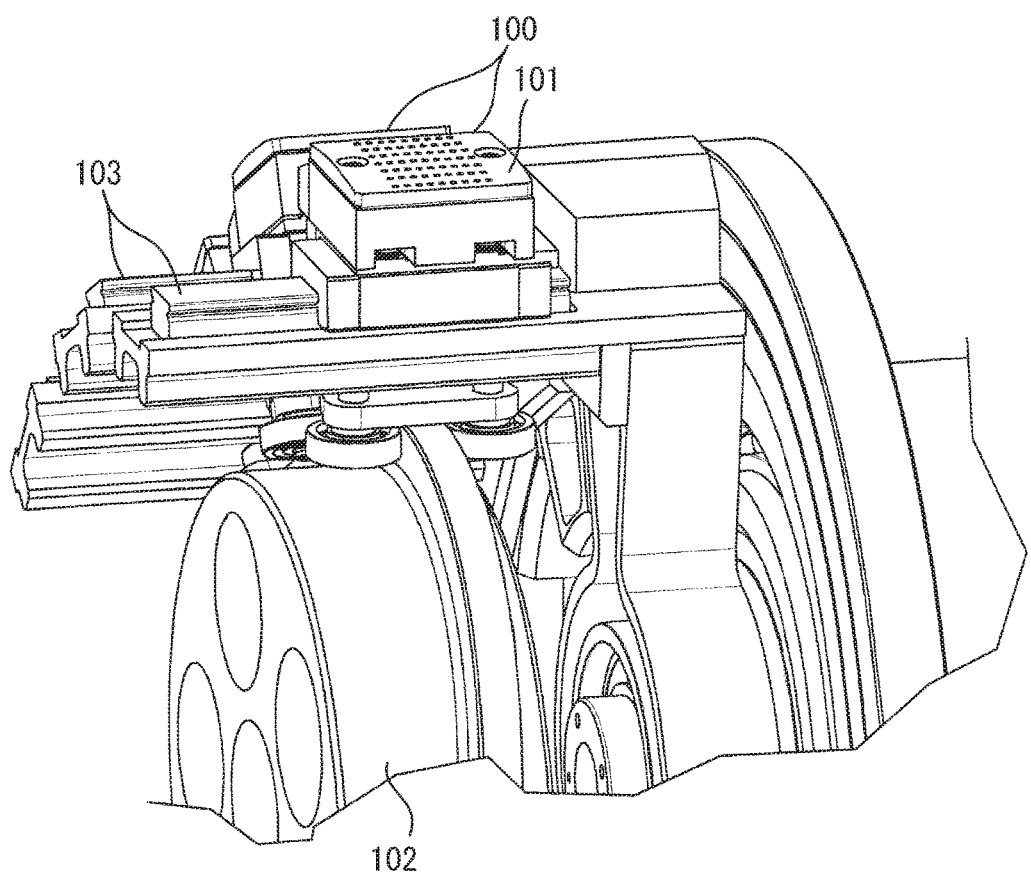
FIG. 10 is a perspective view showing a part of a manufacturing device known in the art.

FIG. 9C and FIG. 9D show still another example.

In these figures, the fifth pulley 15 and the sixth pulley 16 have different diameters from each other. Therefore, the rotation speed of the second pulley 12 is changed by the transmission mechanism SC to a speed that is different from the rotation speed of the third pulley 13.

When changing the size, the fifth and sixth pulleys 15, 16 of FIG. 9C are switched around as shown in FIG. 9D. That is, the speed ratio is set to the first speed ratio when manufacturing a diaper of the first, small size, and to the second speed ratio when manufacturing a diaper of the second, large size.

Note that in this example, only one of the fifth and sixth pulleys may be changed to a pulley of a different diameter.

While preferred embodiments have been described above with reference to the drawings, obvious variations and modifications will readily occur to those skilled in the art upon reading the present specification.

For example, the transmission mechanism may be used to increase the interval between web pieces other than side panels.

The transmission mechanism may be implemented by a combination of gears, instead of belts and pulleys.

The worn article may be of a diaper type or a pants type.

Thus, such changes and modifications are deemed to fall within the scope of the present invention, which is defined by the appended claims.

INDUSTRIAL APPLICABILITY

The present invention is applicable to a method for manufacturing a disposable worn article, and to manufacturing of a device for manufacturing the same.

REFERENCE SIGNS LIST

1: Interval-increasing unit, 1B: First belt, 1S: First mover
10: Frame, 11 to 17: First to seventh pulleys
2B: Second belt, 2S: Second mover
20: Absorbent body portion, 20b: Rear torso portion, 20c: Crotch portion, 20f: Front torso portion
21: Tab member
3: First re-pitch drum, 3B: Third belt, 2T, 3T: Tensioner
4: Interval-increasing drum (second re-pitch drum), 4L, 4R: Left and right pads
40: Rotor, 41: Link mechanism, 42: Cam drum, 43, 44: Link
5R: Slider
51, 52: First and second rollers
51P, 52P: First and second pads
C: Cut-off line, CL: Center line
F1: First touch fastener
PL, PR: Side panel (sheet piece)
P1, P1: Interval, P2: Set-to-set interval, P11: Receiving position
P21: Hand-over position
SC: Transmission mechanism
X: Width direction (axial direction), Y: Flow direction
W: Continuous web

The invention claimed is:

1. A device for manufacturing a disposable worn article, the device comprising:
a cam drum; and
a rotor that is rotated around the cam drum, wherein:
the rotor includes a plurality of units; and
each of the units includes:
a mover that is guided by the cam drum and reciprocates in an axial direction parallel to an axial line of the cam drum by virtue of the rotation of the rotor;
a first belt connected to the mover;
a first pulley and a second pulley between which the first belt is wound and which rotate together with the first belt;
a pad that reciprocates in the axial direction in accordance with the reciprocation of the mover, while holding a sheet piece, which is a part of the worn article;
a second belt linked to the pad;
a third pulley and a fourth pulley between which the second belt is wound and which rotate together with the second belt; and
a transmission mechanism that transmits the rotation of the second pulley to the third pulley and changes a speed of reciprocation of the pad with respect to a speed of reciprocation of the mover.

2. The device for manufacturing a disposable worn article according to claim 1, wherein the transmission mechanism is present between the second pulley and the third pulley, and changes a rotation speed of the third pulley with respect to a rotation speed of the second pulley, thereby changing the speed of reciprocation of the pad with respect to the speed of reciprocation of the mover.

3. The device for manufacturing a disposable worn article according to claim 2, wherein the transmission mechanism comprises:
a fifth pulley to which a torque of the second pulley is input;
an endless third belt that is wound around the fifth pulley and is driven by the rotation of the fifth pulley; and
a sixth pulley around which the third belt is wound, which is rotated by the rotation of the third belt, and which inputs a torque thereof to the third pulley.

4. The device for manufacturing a disposable worn article according to claim 3, wherein the transmission mechanism further comprises at least one of a seventh pulley that is placed on the same axis with the fifth pulley and has a diameter different from the fifth pulley, and a seventh pulley that is placed on the same axis with the sixth pulley and has a diameter different from the sixth pulley.

5. The device for manufacturing a disposable worn article according to claim 3, further comprising a tensioner for adjusting a tension of the third belt.

6. A disposable worn article manufacturing method for manufacturing worn articles of a first size and a second size by using the manufacturing device according to claim 1, the method comprising the steps of:
setting the transmission mechanism to a first speed ratio when manufacturing a worn article of the first size; and
setting the transmission mechanism to a second speed ratio different from the first speed ratio when manufacturing a worn article of the second size.

7. A disposable worn article manufacturing method for manufacturing worn articles of a first size and a second size by using the manufacturing device according to claim 1, the method comprising the step of changing a speed ratio of the transmission mechanism when changing a size of the worn article to be manufactured.

8. A disposable worn article manufacturing method for manufacturing worn articles of a first size and a second size by using the manufacturing device according to claim 3, the method further comprising:

when changing a size of the worn article to be manufactured, at least one of the step of changing the fifth pulley to another fifth pulley having a different diameter and the step of changing the sixth pulley to another sixth pulley having a different diameter.

9. The device for manufacturing a disposable worn article according to claim 4, further comprising a tensioner for adjusting a tension of the third belt.

10. A disposable worn article manufacturing method for manufacturing worn articles of a first size and a second size by using the manufacturing device according to claim 2, the method comprising the steps of:

setting the transmission mechanism to a first speed ratio when manufacturing a worn article of the first size; and setting the transmission mechanism to a second speed ratio different from the first speed ratio when manufacturing a worn article of the second size.

11. A disposable worn article manufacturing method for manufacturing worn articles of a first size and a second size by using the manufacturing device according to claim 2, the method comprising the step of changing a speed ratio of the transmission mechanism when changing a size of the worn article to be manufactured.

* * * * *